US012611383B1

(12) United States Patent
Welin-Berger

(10) Patent No.: US 12,611,383 B1
(45) Date of Patent: Apr. 28, 2026

(54) PHARMACEUTICAL COMPOSITIONS FOR TREATING MCT8 DEFICIENCY

(71) Applicant: Rare Thyroid Therapeutics International AB, Stockholm (SE)

(72) Inventor: Katayoun Welin-Berger, Södertäljer (SE)

(73) Assignee: Rare Thyroid Therapeutics International AB, Stockholm (SE)

(*) Notice: Subject to any disclaimer, the term of this patent is extended or adjusted under 35 U.S.C. 154(b) by 0 days.

(21) Appl. No.: 19/261,360

(22) Filed: Jul. 7, 2025

(51) Int. Cl.
*A61K 9/20* (2006.01)
*A61K 9/00* (2006.01)
*A61K 31/192* (2006.01)

(52) U.S. Cl.
CPC .......... *A61K 9/2059* (2013.01); *A61K 9/0095* (2013.01); *A61K 9/2009* (2013.01); *A61K 9/2018* (2013.01); *A61K 31/192* (2013.01)

(58) Field of Classification Search
CPC ...... A61K 9/00; A61K 9/2059; A61K 9/0095; A61K 9/2009; A61K 9/2018; A61K 31/00; A61K 31/192
See application file for complete search history.

(56) References Cited

U.S. PATENT DOCUMENTS 12,466,781 B2 11/2025 von Geldern et al.

OTHER PUBLICATIONS

Rare Disease Research, MCT8 Deficient (Allan-Herndon-Dudley Syndrome), https://www.rarediseaseresearch.com/mct8-deficiency, 4 pages. (Year: 2022).*
Ph. Eur. 2.9.40. Uniformity of Dosage Units European Pharmacopoeia, Edition 5.2; pp. 3117-3120; 2005.
Tiratricol Certificate of Analysis, Apr. 2024.
Doldan C., et al., "Dicalcium Phosphate Dihydrate and Anhydrous Dicalcium Phosphate for Direct Compression: A Comparative Study," International Journal of Pharmaceutics, Sep. 1995, vol. 124 (1), pp. 69-74.
CAS Registry No. 7757-93-9 (Accessed from https://scifindern.cas.org/searchDetail/substance/685af88ab14bed4ecfb2d597/ substance Details on Jun. 24, 2025, 2 pages).
CAS Registry No. 7789-77-7 (Accessed from https://scifindern.cas.org/searchDetail/substance/685af72cb14bed4ecfb2c78f/ substance Details on Jun. 24, 2025, 2 pages).
Maclean, et al.; Exploring the Performance-Controlling Tablet Disintegration Mechanisms for Direct Compression Formulations. International Journal of Pharmaceutics. 599. 120221. 10.1016/j.ijpharm.2021.120221; Apr. 15, 2021.
Emcitate Orphan Maintenance Assessment Report: Treatment of Allan-Herndon-Dudley syndrome EU/3/17/1945, Mar. 11, 2025, 8 pages.
Emcitate EPAR—Public assessment report; International non-proprietary name: Tiratricol Procedure No. EMEA/H/C/005220/0000; Mar. 11, 2025, 111 pages.
CHMP summary of positive opinion for Emcitate; EMA/49758/2025; First published: Dec. 13, 2024; Last updated: Mar. 11, 2025; 2 pages.
Emcitate EPAR—All authorised presentations; Mar. 11, 2025; 1 page.
Emcitate EPAR—An overview of Emcitate and why it is authorised in the EU; EMA/1545/2025; EMEA/H/C/005220; 3 pages; Mar. 11, 2025.
Emcitate EPAR—EU Risk Management Plan (RMP) for Emcitate (tiratricol); 38 pages; Mar. 11, 2025.
Emcitate : EPAR—Product information Emcitate 350 microgram dispersible tablets; 27 pages; Mar. 11, 2025.
ClinicalTrials: "Thyroid Hormone Analog Therapy in MCT8 Deficiency: Triac Trial Patients," ClinicalTrials.gov ID: NCT02060474, Revised on Apr. 12, 2019, 16 Pages, Retrieved from URL: https://clinicaltrials.gov/study/NCT02060474term=NCT02060474&rank=1.
Egetis Therapeutics: "An Integrated Orphan Drug Company, Focusing on Latestage Development for Commercialization," Corporate Presentation, Aug. 2022, 63 Pages.
Egetis Therapeutics, "An integrated orphan drug company, focusing on late-stage development for commercialization", Corporate Presentation, dated Jul. 2023, 82 pages.
Emcitate® (tiratricol) Medical and Product Information, manufacturer: Cenexi, version No. EmTIVer005, revised: Nov. 2021; 6 pages.
EU Clinical Trials Register; EudraCT No. 2014-000178-20, retrieved online at https://www.clinicaltrialsregister.eu/ctr-search/trial/2014-000178-20/DE on Mar. 21, 2024; 5 pages.
EU Clinical Trials Register; EudraCT No. 2019-003370-35, retrieved online at https://www.clinicaltrialsregister.eu/ctr-search/trial/2019-003370-35/GB on Mar. 21, 2024; 5 pages.
Freund, M. et al., "Effects of Tiratricol Treatment Withdrawal in Monocarboxylate Transporter 8 (MCT8) Deficiency: ReTRIACt Trial", ESPE document, 1 page, (2023).
Groeneweg, S. et al., "Disease characteristics of MCT8 deficiency: an international, retrospective, multicentre cohort study", Lancet Diabetes Endocrinol., 8(7):594-605, (2020).
Groeneweg, S. et al., "Effectiveness and safety of the tri-iodothyronine analogue Triac in children and adults with MCT8 deficiency: an international, single-arm, open-label, phase 2 trial", Lancet Diabetes Endocrinol., retrieved from http://dx.doi.org/10.1016/S2213-8587(19)30155-X, (published online: Jul. 31, 2019), 12 pages.
Groeneweg, S. et al., "Supplementary appendix: Effectiveness and safety of the tri-iodothyronine analogue Triac in children and adults with MCT8 deficiency: an international, single-arm, open-label, phase 2trial", Lancet Diabetes Endocrinol 2019; published online Jul. 31, 2019 at http://dx.doi.org/10.1016/S2213-8587(19)30155-X; 284 pages.
Groeneweg, S. et al., Supplementary methods, results, figures, and tables. Retrieved on Dec. 9, 2024, 22 pages.

(Continued)

*Primary Examiner* — D. L. Jones
(74) *Attorney, Agent, or Firm* — Charles C. Achkar; Amster Rothstein & Ebenstein LLP

(57) ABSTRACT

Provided are pharmaceutical compositions of tiratricol and/or salts thereof, and methods of use thereof.

19 Claims, 8 Drawing Sheets

(56) References Cited

OTHER PUBLICATIONS

Groeneweg, S. et al., Supplementary methods, results, figures, and tables. Retrieved on Dec. 9, 2024, 28 pages.
Triacana® (Triac—Tiratricol) Product Label; Manufacterer: SIDUS; 2024; 2 pages.
Van Geest, F. et al., “Long-Term Efficacy of T3 Analogue Triac in Children and Adults With MCT8 Deficiency: A Real-Life Retrospective Cohort Study”, J Clin Endocrinol Metab., 107(3):e1136-47, (2022).
Van Geest, F. et al., “Supplementary material to Long-Term Efficacy of T3 Analogue Triac in Children and Adults With MCT8 Deficiency: A Real-Life Retrospective Cohort Study”, J Clin Endocrinol Metab., 18 pages, (2021).
Emcitate 350 microgram dispersible tablets—tiratricol on sale by Rare Thyroid Therapeutics International AB in Germany on May 1, 2025.
Package leaflet: Information for the patients in Germany—Emcitate 350 microgram dispersible tablets—tiratricol; Made available on Mar. 11, 2025.
Emcitate 350 microgram dispersible tablets—tiratricol on sale by Rare Thyroid Therapeutics International AB in France on May 15, 2025.
Package leaflet: Information for the patients in France—Emcitate 350 microgram dispersible tablets—tiratricol; Made available on Mar. 11, 2025.
Emcitate 350 micrograms tablets—tiratricol made available or on sale by Rare Thyroid Therapeutics International AB under the early access programme on Oct. 15, 2014.
Package leaflet: Information for patient—Emcitate 350 micrograms tablets- tiratricol Made available under the early access programme on Mar. 9, 2020.
Gazek N, Feller AL, Vaiani E, Di Palma I, Savransky A, Ramírez P, Marino R, Pérez Garrido N, Lazzati JM, Herzovich V, Dujovne N. Treatment with TRIAC in pediatric patients with MCT8. Arch Argent Pediatr. Dec. 1, 2023;121(6):e202202968. English, Spanish. doi: 10.5546/aap.2022-02968.eng. Epub Mar. 16, 2023. PMID: 36883873.
Ünsal Y, Hayran G. Impact of Early Intervention with Triiodothyroacetic Acid on Peripheral and Neurodevelopmental Findings in a Boy with MCT8 Deficiency. J Clin Res Pediatr Endocrinol. Mar. 11, 2024;16(1):116-122. doi: 10.4274/jcrpe.galenos.2023.2023-10-1. Epub Dec. 6, 2023. PMID: 38054413; PMCID: PMC10938514.
Groeneweg S., et al. Effectiveness and safety of the tri-iodothyronine analogue Triac in children and adults with MCT8 deficiency: an international, single-arm, open-label, phase 2 trial. Lancet Diabetes Endocrinol. Sep. 2019;7(9):695-706. doi: 10.1016/S2213-8587(19)30155-X. Epub Jul. 31, 2019. PMID: 31377265; PMCID: PMC7611958.
Van Geest FS, et al, Visser WE. Long-Term Efficacy of T3 Analogue Triac in Children and Adults With MCT8 Deficiency: A Real-Life Retrospective Cohort Study. J Clin Endocrinol Metab. Feb. 17, 2022;107(3):e1136-e1147. doi: 10.1210/clinem/dgab750. PMID: 34679181; PMCID: PMC8852204.

* cited by examiner

Error bars represent ± standard deviation.

Error bars represent ± standard deviation

Error bars represent ± standard deviation.

Error bars represent ± standard deviation.

Error bars represent ± standard deviation

Error bars represent ± standard deviation

Error bars represent standard deviation

PHARMACEUTICAL COMPOSITIONS FOR TREATING MCT8 DEFICIENCY

MCT8 deficiency is a rare, X-linked disorder caused by mutations in the thyroid hormone transporter MCT8. Patients with MCT8 deficiency typically have profound early neurodevelopmental impairment and peripheral thyrotoxicosis. Symptoms of this disorder usually present after the first 2-3 months of life, characterized by hypotonia (lack of head lift), developmental delay, and failure to thrive. Over time, their symptoms become progressively severe and include cognitive issues, gross and fine motor delay, movement disorders such as hypokinesia and dystonia, mixed hypotonia with axial spasticity, limited ability to communicate, lack of weight gain, lack of increase in muscle tone, sleep problems, thyroid hormone abnormalities, and cardiac complications, alongside the presenting symptoms.

With no approved medical treatments for MCT8 deficiency, management is primarily focused on supportive care including nutritional support, physical and occupational therapy for neuromuscular dysfunction and medication to manage complications (e.g. antiepileptic medication).

Tiratricol is an endogenous available metabolite of thyroid hormone, with similar bioactive properties as T3. Tiratricol enters the cell independently of MCT8, bypassing the pathophysiologic defect in MCT8 deficiency. Clinical trials for the use of tiratricol for the treatment of MCT8 deficiency are ongoing. Tiratricol has previously been sold in a tablet form as Teatrois.

Generally, scored tablets facilitate optimum dose control of patients and assure flexibility in prescription. However, Rodenhuis, et al., observed that, in 1998, European regulatory authorities started a policy to discourage scoring of tablets. N. Rodenhuis et al., "The rationale of scored tablets as dosage form." European J. of Pharmaceutical Sciences 21 (2004):305-308. Rodenhuis, et al., attributed the new policy to reports of "bad functioning score lines," "tablets difficult to break," and "unsatisfactory mass uniformity of the subdivided halves." Rodenhuis, et al. noted that "[i]mproving the functioning of score lines may be a more practical approach than banning this [scored] dosage form".

Moreover, in a report by Peek et al., "elderly patients" aged 50-79 using, without specific instruction, mechanical tablet splitters to break scored tablets produced highly unsatisfactory division of the tablets. Peek, B. T., Al-Achi, A., Coombs, S. J. "Accuracy of Tablet Splitting by Elderly Patients." The Journal of the American Medical Association 288 No. 4 (2002):139-145. Peek, et al. found warfarin 5 mg was, on average, split into 1.9 and 3.1 mg tablets when a mechanical tablet splitter was used. This potent anticoagulant has such a narrow therapeutic range that 2.0, 2.5, and 3 mg tablet doses are manufactured. Biron, et al., demonstrated that warfarin 10 mg also often split to less than 4.25 or greater than 5.75 mg. Biron, C., Liczner, P., Hansel, S., Schved, J. F., "Oral Anticoagulant Drugs: Do Not Cut Tablets in Quarters." Thromb Haemost 1201 (1999). In addition, a statistically significant loss of mass resulted from crumbling or chipping when breaking the tablets.

There is a need for a pharmaceutical composition of tiratricol with improved dissolution properties and that can be accurately divided. The present disclosure fulfills these and other needs, as evident in reference to the following disclosure.

SUMMARY

Figure 1:
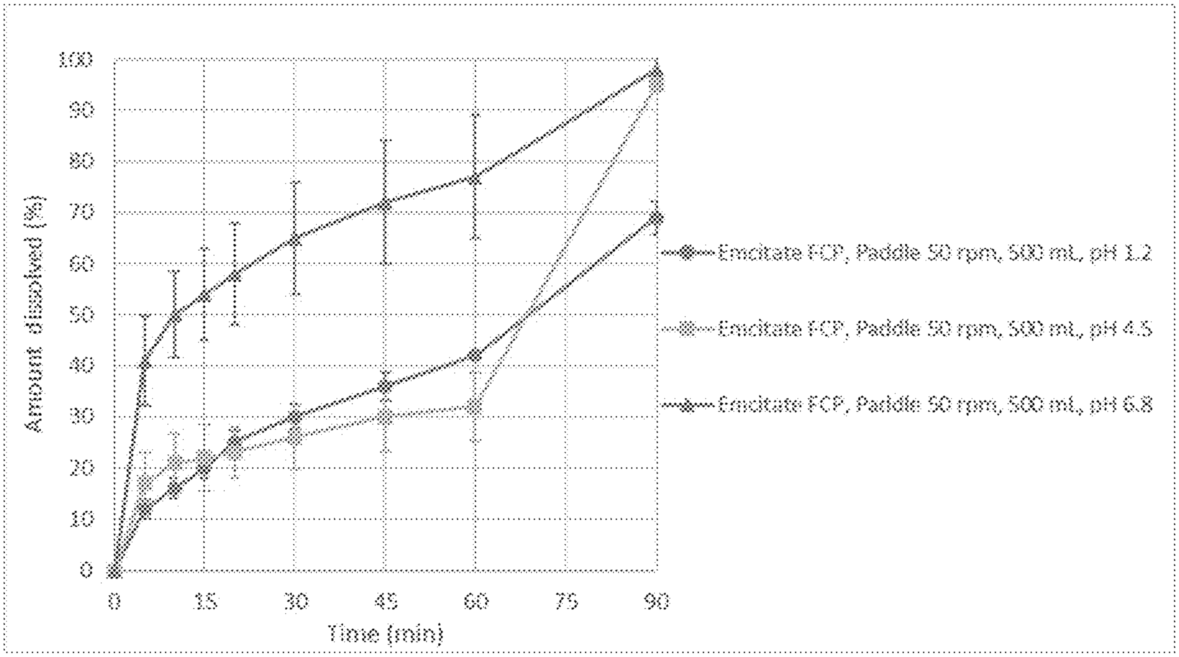
FIG. 1 shows the dissolution of Emcitate FCP (Batch EF0078) in pH 1.2, pH 4.5 and pH 6.8 buffer media (500 mL) using Apparatus 2 at 50 rpm (n=6).

Provided is a pharmaceutical composition comprising:

compound 1, or a pharmaceutically acceptable salt thereof, in an amount of about 0.2%;

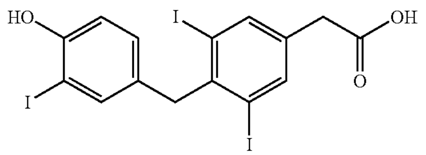

(1)

calcium hydrogen phosphate anhydrous in an amount of between about 67% to about 77%;

maize starch in an amount of about 15%;

lactose monohydrate in an amount of between about 5% to about 15%; and magnesium stearate in an amount of between about 2% to about 3%.

Also provided is a method of treating a MTC8 deficiency disorder in an individual, comprising administering to the individual in need thereof, a therapeutically acceptable amount of a pharmaceutical composition described herein.

These and other aspects of the invention will be apparent upon reference to the following detailed description. To this end, various references are set forth herein which describe in more detail certain background information, procedures, compounds, and/or compositions, and are each hereby incorporated by reference in their entirety.

DETAILED DESCRIPTION

Provided is a pharmaceutical composition comprising:

compound 1, or a pharmaceutically acceptable salt thereof, in an amount of about 0.2%;

(1)

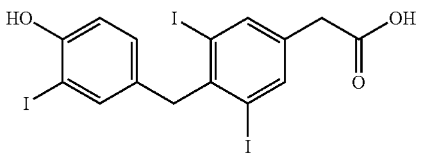

calcium hydrogen phosphate anhydrous in an amount of between about 67% to about 77%;

maize starch in an amount of about 15%;

lactose monohydrate in an amount of between about 5% to about 15%; and magnesium stearate in an amount of between about 2% to about 3%.

In some embodiments, compound 1, or a pharmaceutically acceptable salt thereof, is present in an amount of about 350 μg, based on the weight of the free acid.

In some embodiments, the calcium hydrogen phosphate anhydrous is present in an amount of about 72%.

In some embodiments, the lactose monohydrate is present in an amount of about 10%.

In some embodiments, the magnesium stearate is present in an amount of about 2.5%.

In some embodiments, compound 1, or a pharmaceutically acceptable salt thereof, is micronized.

In some embodiments, compound 1, or a pharmaceutically acceptable salt thereof, has a particle size D (95)≤10 μm.

In some embodiments, the pharmaceutical composition is a tablet.

In some embodiments, the pharmaceutical composition is an uncoated tablet.

In some embodiments, the tablet is oblong. In some embodiments, the tablet is about 10 mm long and about 5 mm wide.

In some embodiments, the scored tablet is single-sided scored. In some embodiments, the scored tablet is double-sided scored. Such a scored dosage form allows for the ready fractionation of the tablet resulting in two or more subparts of the tablet, each subpart containing a smaller dose than the complete tablet so that fractional doses can be administered. For example, tablets can be scored into two halves (each half containing half of the dose of the tablet).

In some embodiments, the scored tablet has one or more of the following properties:

the mass loss after split is less than 3.0%, the friability of the split is not more than 1.0%, the split content uniformity meets the USP<905>requirement, the split dissolution and the complete tablet are similar, and the split is stable in a medical medicine storage box/bottle for at least 3 months.

In some embodiments, the mass loss after split is less than 3.0%. In some embodiments, the friability of the split is not more than 1.0%. In some embodiments, the split content uniformity meets the USP<905>requirement. In some embodiments, the split dissolution and the complete tablet are similar. In some embodiments, the split is stable in a medical medicine storage box/bottle for at least 3 months.

In some embodiments, the scored tablet has all of the following properties:

the mass loss after split is less than 3.0%, the friability of the split is not more than 1.0%, the split content uniformity meets the USP<905>requirement, the split dissolution and the complete tablet are similar, and the split is stable in a medical medicine storage box/bottle for at least 3 months.

In some embodiments, the scored tablet can be divided using a mechanical dividing mode. In some embodiments, the scored tablet can be divided using a direct manual breaking is adopted.

In some embodiments, the tablet is about 10 mm long and about 5 mm wide with score lines on both sides.

In some embodiments, the pharmaceutical composition has a content uniformity of between about 95% and about 105%.

In some embodiments, the pharmaceutical composition has an acceptance value less than 15 in content uniformity testing according to USP<905>uniformity of dosage units.

In some embodiments, the pharmaceutical composition has a relative standard deviation (RSD) of about 6 or less in content uniformity testing according to USP<905>.

In some embodiments, the pharmaceutical composition has content uniformity in accordance with Ph. Eur. 2.9.40.

In some embodiments, the pharmaceutical composition dissolves in 10 minutes or less under the following parameters: Apparatus 1 (basket); 100 rpm rotation speed; 500 mL volume of a dissolution media that is pH 6.8 phosphate buffer, at 37° C.

In some embodiments the composition does not include calcium hydrogen phosphate dihydrate.

Also provided is a method of treating a MTC8 deficiency disorder in an individual, comprising administering to the individual in need thereof, a therapeutically acceptable amount of a pharmaceutical composition described herein.

In some embodiments, the MCT8 deficiency disorder is Allan-Herndon-Dudley syndrome.

In some embodiments, the pharmaceutical composition is suspended in water prior to administration. In some embodiments, the tablets do not need to be crushed or ground before suspension. In some embodiments, the volume of water used to suspend the tablets is adjusted to each individual dose.

In some embodiments, the pharmaceutical composition is administered through a PEG tube. In some embodiments, when administering through a PEG tube, the pharmaceutical composition is suspended in water and given through the tube and the tube is then flushed with water.

| Amount of Compound 1 (mcg) | Volume for Suspension (mL) | Flush Volume for Administration Through PEG Tube (mL) | Total Volume Administered (mL) |
|---|---|---|---|
| 350-1,400 | 30 | 10 | 40 |
| 1,750-2,450 | 45 | 10 | 55 |
| 2,800-3,150 | 60 | 10 | 70 |

In some embodiments, the dose being administered is individually adjusted based on serum TSH levels, (F) T4 and T3 levels of the individual.

In some embodiments, administration comprises an individualized dose titration schedule based on the following schedule:

| Dose Level | Compound 1 Dose (μg) | Regimen |
|---|---|---|
| 1 | 350 | 350 μg once daily |
| 2 | 700 | 350 μg twice daily |
| 3 | 1050 | 350 μg three times daily |
| 4 | 1400 | 700 μg/350 μg/350 μg |
| 5 | 1750 | 700 μg/350 μg/700 μg |
| 6 | 2100 | 700 μg/700 μg/700 μg |
| 7 | 2450+ | Increasing in 350 or 700 μg increments |

Clinical experience in MCT8 deficiency with dose titration demonstrated that a maintenance dose for patients over 10 kg of body weight is frequently between 700-2100 micrograms (2-6 tablets of 350 micrograms) per day divided into 1-3 administrations.

Definitions

In this description, certain specific details are set forth in order to provide a thorough understanding of various embodiments. However, one skilled in the art will understand that the invention may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed invention.

Reference throughout this specification to "one embodiment" or "an embodiment" or "some embodiments" or "a certain embodiment" means that a particular feature, structure or characteristic described in connection with the embodiment is included in at least one embodiment. Thus, the appearances of the phrases "in one embodiment" or "in an embodiment" or "in some embodiments" or "in a certain embodiment" in various places throughout this specification are not necessarily all referring to the same embodiment. Furthermore, the particular features, structures, or characteristics may be combined in any suitable manner in one or more embodiments.

Also, as used in this specification and the appended claims, the singular forms "a," "an," and "the" include plural referents unless the content clearly dictates otherwise.

As used herein, "tiratricol" may be referred to as compound 1, EMCITATE, TRIAC or 3,3',5-triiodothyroacetic acid and has the following chemical structure:

(1)

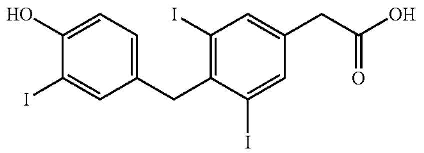

Tiratricol and its pharmaceutically acceptable salts may form solvates, including hydrates. Solvates formed by the incorporation into the solid-state structure (e.g. crystal structure) of the compounds and salts described herein of molecules of a non-toxic pharmaceutically acceptable solvent. Examples of such solvents include water, alcohols (such as ethanol, isopropanol and butanol) and dimethylsulfoxide. Solvates can be prepared by recrystallizing the compounds and salts with a solvent or mixture of solvents containing the solvating solvent. Whether or not a solvate has been formed in any given instance can be determined by subjecting crystals to analysis using well known and standard techniques such as thermogravimetric analysis (TGA), differential scanning calorimetry (DSC) and X-ray crystallography. The solvates can be stoichiometric or nonstoichiometric solvates. In some embodiments, the solvate is a hydrate, such as a hemihydrate, monohydrate, or dihydrate.

As used herein, a"scored tablet" (also referred to as "dividing tablet") has a continuous indentations through the surface of the tablet for dividing the tablet into smaller subunits. The problems of the existing forms of scored tablets are well known. These problems include loss of active drug, inaccurate breaking of tablets, large friability of broken pieces or poor stability, etc., so that breaking of tablets is often less than ideal. Moreover, for different medicines, the properties of materials are different, so that the difficulty of breaking off is different. Breaking the wafer can enhance the compliance of clinical administration for dysphagia patients or to meet the treatment of patients who need non-full tablet quantities.

As used herein, "about" generally means±20% of the stated value, and includes more specifically values of ±10%, ±5%, ±2% and ±1% of the stated value. In terms of components of the pharmaceutical composition (such as the amount of compound 1), "about" means±2% of the stated value and, in some embodiments, +1% of the stated value.

As used herein, "administering to a patient" refers to the process of introducing a composition or dosage form into the patient via an art-recognized means of introduction.

As used herein, "adjusting administration", "altering administration", "adjusting dosing", or "altering dosing" are all equivalent and mean tapering off, reducing or increasing the dose of the substance, ceasing to administer the substance to the patient, or substituting a different active agent for the substance.

As used herein, "co-administer" and "co-administration" and variants thereof mean the administration of at least two drugs to a patient either subsequently, simultaneously, or consequently proximate in time to one another (e.g., within the same day, or week or period of 30 days, or sufficiently proximate that each of the at least two drugs can be simultaneously detected in the blood plasma). When co-administered, two or more active agents can be co-formulated as part of the same composition or administered as separate formulations. This also may be referred to herein as "concomitant" administration or variants thereof.

As used herein, "amelioration of the symptoms" of a particular disorder by administration of a particular pharmaceutical composition refers to any lessening, whether permanent or temporary, lasting or transient, that can be attributed to or associated with administration of the composition.

As used herein, "baseline" refers to the period of time just prior to initiation of therapy. The patient's condition just prior to initiation of therapy can be referred to as the patient's baseline condition.

As used herein, "detectable amount" means a quantity that is above the detection limit of the apparatus or assay used to quantify the amount of the substance being measured such that the presence of the substance can be confirmed with a high degree of statistical significance (e.g. 99% confidence). In certain embodiments, a "detectable amount"

is greater than 0.10%, greater than 0.05%, greater than 0.01%, or greater than 0.001%.

As used herein the term "disorder" is intended to be generally synonymous, and is used interchangeably with, the terms "disease," "syndrome," and "condition" (as in medical condition), in that all reflect an abnormal condition of the human or animal body or of one of its parts that impairs normal functioning, is typically manifested by distinguishing signs and symptoms.

As used herein, a "dosage" is the prescribed administration of a specific amount, number, and frequency of doses over a specific period of time.

As used herein, a "dose" means the measured quantity of an active agent to be taken at one time by a patient. In certain embodiments, wherein the active agent is not a free base, the quantity is the molar equivalent to the corresponding amount of free base.

As used herein, "dosing regimen" means the dose of an active agent taken at a first time by a patient and the interval (time or symptomatic) at which any subsequent doses of the active agent are taken by the patient such as from about 20 to about 160 mg once daily, e.g., about 20, about 40, about 60, about 80, about 100, about 120, or about 160 mg once daily. The additional doses of the active agent can be different from the dose taken at the first time.

As used herein, "down-titration" of a compound refers to decrease the amount of a compound to achieve a therapeutic effect that occurs before dose-limiting intolerability for the patient. Down-titration can be achieved in one or more dose increments, which may be the same or different.

As used herein, "effective amount" and "therapeutically effective amount" of an agent, compound, drug, composition, or combination is an amount which is nontoxic and effective for producing some desired therapeutic effect upon administration to a subject or patient (e.g., a human subject or patient). The precise therapeutically effective amount for a subject may depend upon, e.g., the subject's size and health, the nature and extent of the condition, the therapeutics or combination of therapeutics selected for administration, and other variables known to those of skill in the art. The effective amount for a given situation is determined by routine experimentation and is within the judgment of the clinician.

As used herein, "informing" means referring to or providing published material, for example, providing an active agent with published material to a user; or presenting information orally, for example, by presentation at a seminar, conference, or other educational presentation, by conversation between a pharmaceutical sales representative and a medical care worker, or by conversation between a medical care worker and a patient; or demonstrating the intended information to a user for the purpose of comprehension.

As used herein, "labeling" means all labels or other means of written, printed, graphic, electronic, verbal, or demonstrative communication that is upon a pharmaceutical product or a dosage form or accompanying such pharmaceutical product or dosage form.

As used herein, the terms "manage," "managing" and "management" refer to preventing or slowing the progression, spread or worsening of a disease or disorder, or of one or more symptoms thereof. Often, the beneficial effects that a subject derives from a prophylactic and/or therapeutic agent do not result in a cure of the disease or disorder. In this regard, the term "managing" encompasses treating a subject who had suffered from the particular disease in an attempt to prevent or minimize the recurrence of the disease.

As used herein, "a medical care worker" means a worker in the health care field who may need or utilize information regarding an active agent, including a dosage form thereof, including information on safety, efficacy, dosing, administration, or pharmacokinetics. Examples of medical care workers include physicians, pharmacists, physician's assistants, nurses, aides, caretakers (which can include family members or guardians), emergency medical workers, and veterinarians.

As used herein, "Medication Guide" means an FDA-approved patient labeling for a pharmaceutical product conforming to the specifications set forth in 21 CFR 208 and other applicable regulations which contains information for patients on how to safely use a pharmaceutical product. A medication guide is scientifically accurate and is based on, and does not conflict with, the approved professional labeling for the pharmaceutical product under 21 CFR 201.57, but the language need not be identical to the sections of approved labeling to which it corresponds. A medication guide is typically available for a pharmaceutical product with special risk management information.

As used herein, "patient" or "individual" or "subject" means a mammal, including a human, for whom or which therapy is desired, and generally refers to the recipient of the therapy.

As used herein, "pharmaceutically acceptable" refers to a material that is not biologically or otherwise undesirable, i.e., the material may be incorporated into a pharmaceutical composition administered to a patient without causing any undesirable biological effects or interacting in a deleterious manner with any of the other components of the composition in which it is contained. When the term "pharmaceutically acceptable" is used to refer to a pharmaceutical carrier or excipient, it is implied that the carrier or excipient has met the required standards of toxicological and manufacturing testing or that it is included on the Inactive Ingredient Guide prepared by the U.S. Food and Drug administration. "Pharmacologically active" (or simply "active") as in a "pharmacologically active" (or "active") derivative or analog, refers to a derivative or analog having the same type of pharmacological activity as the parent compound and approximately equivalent in degree.

As used herein, in some embodiments, "pharmaceutically acceptable salt" refers to acid addition salts with an inorganic or an organic acid. Lists of suitable salts are found in WO 87/05297, Johnston et al., published Sep. 11, 1987; Remington's Pharmaceutical Sciences, 17th ed., Mack Publishing Company, Easton, Pa., 1985, p. 1418; and J. Pharm. Sci., 66, 2 (1977), each of which is incorporated herein by reference in its entirety. A reference for the preparation and selection of pharmaceutical salts of the present disclosure is P. H. Stahl & C. G. Wermuth "Handbook of Pharmaceutical Salts," *Verlag Helvetica Chimica Acta*, Zurich, 2002 which is incorporated herein by reference in its entirety. The organic or inorganic acids include, but are not limited to, hydrochloric, hydrobromic, sulfuric, nitric, phosphoric, sulfamic, acetic, trifluoroacetic, trichloroacetic, propionic, hexanoic, cyclopentylpropionic, glycolic, glutaric, pyruvic, lactic, malonic, succinic, sorbic, ascorbic, malic, maleic, fumaric, tartaric, citric, benzoic, 3-(4-hydroxybenzoyl)benzoic, picric, cinnamic, mandelic, phthalic, lauric, methanesulfonic, ethanesulfonic, 1,2-ethane-disulfonic, 2-hydroxyethanesulfonic, benzenesulfonic, 4-chlorobenzenesulfonic, 2-naphthalenesulfonic, 4-toluenesulfonic, camphoric, camphorsulfonic, 4-methylbicyclo[2.2.2]-oct-2-ene-1-carboxylic, glucoheptonic, 3-phenylpropionic, trimethylacetic, tert-butylacetic, lauryl sulfuric, gluconic, benzoic, glutamic, hydroxynaphthoic, salicylic, stearic, cyclohexylsulfamic, quinic, muconic acid, and the like. In some embodiments, “pharmaceutically acceptable salt” refers to base addition salts with an inorganic or an organic base. Inorganic bases which may be used to prepare salts include, for example, sodium, potassium, lithium, ammonium, calcium, magnesium, iron, zinc, manganese, aluminum hydroxides, carbonates, bicarbonates, phosphates, and the like; particularly preferred are the ammonium, potassium, sodium, calcium, and magnesium hydroxides, carbonates, bicarbonates, or phosphates. Organic bases from which may be used to prepare salts include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine.

As used herein, “prevent,” “preventing,” and “prevention” are meant to include a method of delaying and/or precluding the onset of a disorder, disease, or condition, and/or its attendant symptoms; barring a subject from acquiring a disorder, disease, or condition; or reducing a subject’s risk of acquiring a disorder, disease, or condition.

As used herein, a “product” or “pharmaceutical product” means a dosage form of an active agent plus published material, and optionally packaging.

As used herein, “product insert” means the professional labeling (prescribing information) for a pharmaceutical product, a patient package insert for the pharmaceutical product, or a medication guide for the pharmaceutical product.

As used herein, “professional labeling” or “prescribing information” means the official description of a pharmaceutical product approved by a regulatory agency (e.g., FDA or EMA) regulating marketing of the pharmaceutical product, which includes a summary of the essential scientific information needed for the safe and effective use of the drug, such as, for example indication and usage; dosage and administration; who should take it; adverse events (side effects); instructions for use in special populations (pregnant women, children, geriatric, etc.); safety information for the patient, and the like.

As used herein, “published material” means a medium providing information, including printed, audio, visual, or electronic medium, for example a flyer, an advertisement, a product insert, printed labeling, an internet web site, an internet web page, an internet pop-up window, a radio or television broadcast, a compact disk, a DVD, an audio recording, or other recording or electronic medium.

As used herein, “risk” means the probability or chance of adverse reaction, injury, or other undesirable outcome arising from a medical treatment. An “acceptable risk” means a measure of the risk of harm, injury, or disease arising from a medical treatment that will be tolerated by an individual or group. Whether a risk is “acceptable” will depend upon the advantages that the individual or group perceives to be obtainable in return for taking the risk, whether they accept whatever scientific and other advice is offered about the magnitude of the risk, and numerous other factors, both political and social. An “acceptable risk” of an adverse reaction means that an individual or a group in society is willing to take or be subjected to the risk that the adverse reaction might occur since the adverse reaction is one whose probability of occurrence is small, or whose consequences are so slight, or the benefits (perceived or real) of the active agent are so great. An “unacceptable risk” of an adverse reaction means that an individual or a group in society is unwilling to take or be subjected to the risk that the adverse reaction might occur upon weighing the probability of occurrence of the adverse reaction, the consequences of the adverse reaction, and the benefits (perceived or real) of the active agent. “At risk” means in a state or condition marked by a high level of risk or susceptibility. Risk assessment consists of identifying and characterizing the nature, frequency, and severity of the risks associated with the use of a product.

As used herein, “safety” means the incidence or severity of adverse events associated with administration of an active agent, including adverse effects associated with patient-related factors (e.g., age, gender, ethnicity, race, target illness, abnormalities of renal or hepatic function, co-morbid illnesses, genetic characteristics such as metabolic status, or environment) and active agent-related factors (e.g., dose, plasma level, duration of exposure, or concomitant medication).

As used herein, a subject is said to “tolerate” a dose of a compound if administration of that dose to that subject does not result in an unacceptable adverse event or an unacceptable combination of adverse events. One of skill in the art will appreciate that tolerance is a subjective measure and that what may be tolerable to one subject may not be tolerable to a different subject. For example, one subject may not be able to tolerate headache, whereas a second subject may find headache tolerable but is not able to tolerate vomiting, whereas for a third subject, either headache alone or vomiting alone is tolerable, but the subject is not able to tolerate the combination of headache and vomiting, even if the severity of each is less than when experienced alone.

As used herein, “treat,” “treating,” and “treatment” are meant to include alleviating or abrogating a disorder, disease, or condition, or one or more of the symptoms associated with the disorder, disease, or condition; or alleviating or eradicating the cause(s) of the disorder, disease, or condition itself.

As used herein, “up-titration” of a compound refers to increasing the amount of a compound to achieve a therapeutic effect that occurs before dose-limiting intolerability for the patient. Up-titration can be achieved in one or more dose increments, which may be the same or different.

Examples of embodiments of the present disclosure are provided in the following examples. The following examples are presented only by way of illustration and to assist one of ordinary skill in using the disclosure. The examples are not intended in any way to otherwise limit the scope of the disclosure.

EXAMPLES

Example 1: Preparation of the Pharmaceutical Composition

During the manufacturing of clinical batches, it became obvious that there were technical problems with the compressibility of the Teatrois formulation, i.e. it was difficult to obtain tablets with sufficient hardness and friability. This problem was exacerbated when the tablet shape was changed to an oblong tablet to be able to divide the tablet in equal doses. To overcome the problem, a change of the quality of calcium hydrogen phosphate from a dihydrate to an anhydrous form was made, which resulted in tablets with good compressibility and friability. Emcitate FCP has sufficient hardness, acceptable friability and fulfils the Ph. Eur. Subdivision criteria.

| | Teatrois Original product | Emcitate-DEV Clinical formulation | Emcitate FCP |
|---|---|---|---|
| Strength | 350 μg | 350 μg | 350 μg |
| Tablet weight | 200 mg | 200 mg | 200 mg |
| Composition (mg): | | | |
| Tiratricol | 0.350 | 0.350 | 0.350 |
| Calcium hydrogen phosphate, dihydrate | 145 | 145 | — |
| Calcium hydrogen phosphate, anhydrous | — | — | 145 |
| Maize starch | 30.0 | 30.0 | 30.0 |
| Lactose monohydrate | 20.0 | 20.0 | 20.0 |
| Magnesium stearate | 5.00 | 5.00 | 5.00 |

Example 2: Dissolution

The dissolution method development for Emcitate-DEV also included comparisons between Emcitate-DEV and Teatrois. Both these tablet versions showed poor disintegration properties in the dissolution vessel. That led to the development of a dissolution method with Apparatus I (basket), 100 rpm, 900 mL water containing a relatively high concentration of surfactant (2% SDS). However, the Emcitate FCP tablet has improved disintegration properties and coupled with the solubility profile of the molecule, the 2% SDS method was deemed not suitable as a QC method.

TABLE 1

Tiratricol formulations used in dissolution method development.

| Batch Number | Description |
|---|---|
| 146 | Teatrois, 0.35 mg tiratricol tablet |
| P0543 | Emcitate-DEV, 350 μg tablet |
| P0554 | Emcitate FCP, primary stability batch |
| EF0078 | Emcitate FCP, batch containing tiratricol with particle size D(95) < 8.4 μm |
| EF0079 | Emcitate FCP, batch containing tiratricol with larger particle size, D(95) < 18.2 μm |
| EF0080 | Emcitate FCP, batch containing tiratricol with larger particle size, D(100) < 8.9 μm |

Dissolution Method used for Emcitate-Dev

In the initial phase of development of Emcitate, the dissolution method developed for Emcitate-DEV included also testing of Teatrois to compare dissolution behavior for these two formulations. Both tablet versions showed, by visual observation, poor disintegration properties in the dissolution vessel. That led to the development of a dissolution method utilizing a basket apparatus (Apparatus I) as described in Ph. Eur. 2.9.3, and 900 mL dissolution media containing a relatively high concentration of surfactant (2% SDS). The dissolution method was used for both the 350 μg and 100 μg strengths of Emcitate-DEV. Dissolved tiratricol was analyzed by reversed-phase HPLC.

Dissolution Conditions

- Dissolution medium: Sodium dodecyl sulphate 2.0% in water
- Volume: 900 mL
- Rotation speed: 100 rpm
- Temperature: 37.0° C.±0.5° C.

Chromatographic Conditions

- Column: NucleoShell C18, 100 mm×4.6 mm, 2.7 μm, or equivalent

- Flow-rate: 1.0 mL/min
- Injection volume: 100 μL
- Column temperature: 40° C.
- Detection wavelength: 225 nm
- Mobile phase: Methanol/water/acetonitrile/formic acid, 40/40/20/0.1 (v/v)

Method Validation Results

- Specificity: Tiratricol peak well separated from excipients peaks and related substances peaks.
- Linearity: Tiratricol peak area response is linear with r=0.99997
- Accuracy: Recovery of spiked samples 98-101%.
- Precision/Intermediate precision: RSD=3.2%

Dissolution Method Development for Emcitate FCP

The dissolution method was assessed and optimized for Emcitate FCP. Drug substance solubility characteristics across the pH range as well as relevant dissolution parameters such as apparatus, rotation speed, pH and volume of dissolution media were evaluated.

Tiratricol Solubility

Equilibrium solubility (N=3) in the following media was assessed at 37° C. for 24 hours with pH monitoring at start and at the 24 hour timepoint. Samples were prepared by adding 4 mL of media to 10 mg Tiratricol in a glass vial and placed in a 37° C. heater block with shaking (protected from light). After 24 hours, 1 mL of sample was taken from each vial and centrifuged at 15,000 rpm at 37° C. for 5 minutes. Additional dilution steps were carried out to ensure the concentration of samples was within the range of the calibration standards. Data are presented in Table 2.

TABLE 2

Solubility data for tiratricol (Equilibrium, 24 h)

| | Concentration tiratricol | | pH | |
|---|---|---|---|---|
| Media | (μg/mL) | RSD (%) | initial | 24 h |
| 0.1M HCl | 1.2 | 1.7 | 1.1 | 0.9 |
| Acetate buffer | 9.0 | 2.9 | 4.5 | 4.5 |
| Phosphate buffer | 1,212 | 2.1 | 6.8 | 6.8 |
| FaSSIF v1 | 961 | 2.9 | 6.5 | 6.3 |
| FeSSIF v2 | 2032 | 4.8 | 5.8 | 5.8 |
| 0.5% SDS in water[1] | 528 | 2.0 | 8.9 | 5.8 |
| 1% SDS in water[1] | 1,172 | 3.0 | 9.5 | 5.6 |
| 2% SDS in water[1] | 2,199 | 6.9 | 9.5 | 5.4 |

[1] pH measured but not controlled

Tiratricol has two pKa, at 5.6 (carboxylic acid) and 9.0 (phenolic). The considerably higher solubility at pH 6.8 as compared to at lower pH would be related to ionization of the carboxylic group.

pH of Dissolution Media

Initial investigations were conducted to screen aqueous media across the physiological pH range. Investigations at this stage were conducted using the Apparatus 2 (paddle) as preliminary dissolution studies showed that the Emcitate FCP had a very rapid and complete rate of dissolution (≥85% release within 15 minutes) in 900 mL pH 6.8, with a paddle method using a rotation speed of 100 rpm. Recognizing that 100 rpm is unlikely to be an appropriate rotation speed for an Apparatus 2 based a QC method, 50 rpm was selected as the rotation speed for this investigation of media pH. Furthermore, this investigation was conducted in 500 mL dissolution media, to use the smallest feasible volume to maximize final analyte concentration to aid analysis.

The dissolution profiles of Emcitate FCP (Batch EF0078) in 500 mL aqueous media at 3 different pHs across the physiological pH range were investigated at 50 rpm up to 60 minutes followed by an infinity spin (250 rpm) for 30 minutes.

The dissolution of the Emcitate FCP at 50 rpm is slow, variable and incomplete in all three media. The average dissolution achieved was approx. 30% at 30 minutes in 0.1M HCl and pH 4.5 and 65% at 30 minutes in pH 6.8 media. Coning was observed in all media and a significant increase in the amount of tiratricol dissolved was seen following the infinity spin.

At the 45-minute timepoint, tiratricol dissolution was low in 0.1M HCl and pH 4.5 with average release of 36 and 30%, respectively and higher in pH 6.8 at 70% dissolved. The infinity spin (250 rpm) was started once all the 60-minute samples were taken and by 90 minutes there was an increase to 70% dissolved for 0.1M HCl and 100% dissolved for both pH 4.5 and pH 6.8.

The incomplete dissolution in 0.1M HCl is likely due to sink condition not being achieved when using 500 mL due to the low solubility at pH 1.2. However, using 900 mL would not achieve sink condition either so 0.1 M HCl was judged to not be suitable for the QC method for Emcitate FCP.

At pH 4.5 even a small change in media pH would likely result in variable performance due to the change in tiratricol solubility when approaching the pKa. In a separate study after the apparatus had been selected (see Section Apparatus and Rotation Speed), pH 4.5 was tested with conditions that would be optimal for this pH, i.e. Apparatus 1 using 900 mL. A slower rate of release was observed in pH 4.5 as compared to pH 6.8 and after infinity spin at 250 rpm for 30 minutes, the release in pH 4.5 is 86% vs 100% in pH 6.8. Although the complete dose is soluble at pH 4.5, the lower extent in dissolution could be attributed to observations made during the dissolution study that undissolved material was falling from the basket and settling on the bottom of the vessel. This observation coupled with pH 4.5 being about one unit from the pKa of tiratricol demonstrates that a pH 4.5 media-based dissolution method is not suitable as a QC method for Emcitate FCP.

The overall rate of tablet dissolution was highest in the pH 6.8 media when comparing to both 0.1M HCl and pH 4.5 media and additionally the only media where complete dissolution was achieved. Based on these observations, the pH 6.8 media was selected for further evaluation as the media for the QC method as it displayed a complete drug release for the Emcitate FCP tablet versus the other media.

Apparatus and Rotation Speed

The data generated in the investigation of media pH indicated that 50 rpm was not an appropriate rotation speed for a paddle based method due to the coning that occurs resulting in low extent of release and variable dissolution profiles.

Dissolution studies, to confirm an appropriate apparatus and rotation speed were conducted (n=6) using Apparatus 2 (paddle) at 50 rpm and 75 rpm and Apparatus 1 (basket) at 100 rpm, using 500 mL media pH 6.8. The dissolution profiles for Emcitate FCP are shown in FIG. 1.

The rate of dissolution was slow and variable for both 50 rpm and 75 rpm with Apparatus 2 (paddle). Following the 60-minute sampling timepoint, an infinity spin (250 rpm) was initiated and complete release of tiratricol was achieved for both rotation speeds. Coning was again observed during the dissolution study.

Figure 2:
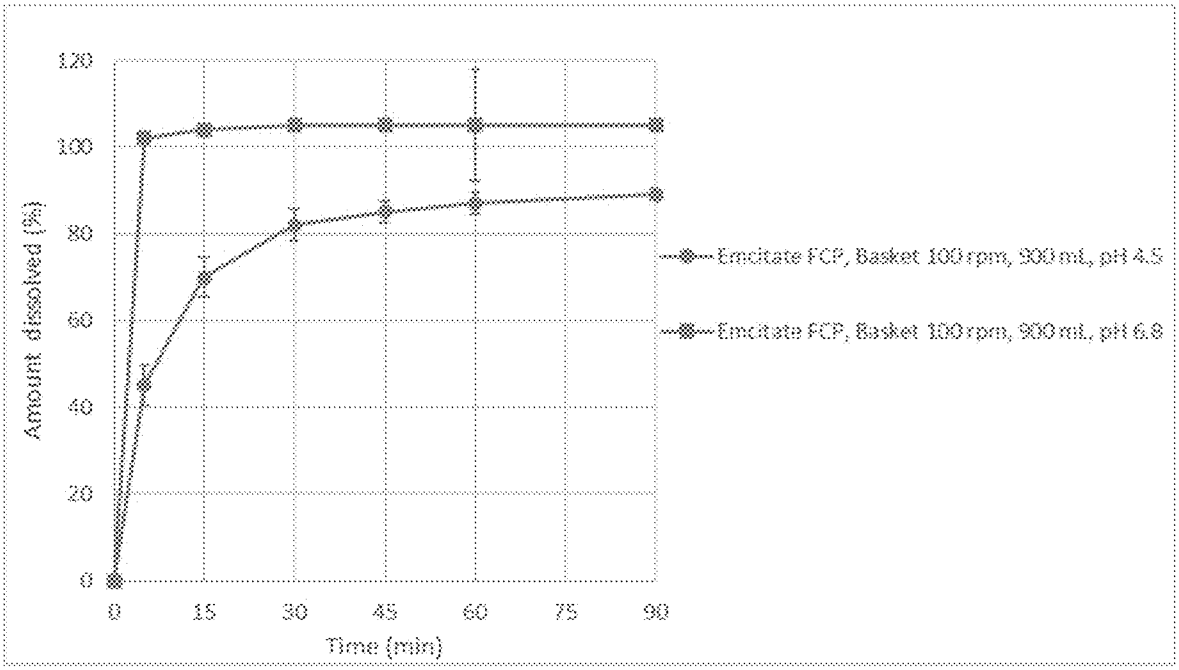
FIG. 2 shows the dissolution of Emcitate FCP (Batch EF0078) in pH 4.5 and pH 6.8 buffer media (900 mL) using Apparatus 1 at 100 rpm (n=6).

Using Apparatus 1 (basket) at 100 rpm, rapid and complete dissolution was observed, and complete release was achieved within 15 minutes. The use of the Apparatus1 (basket) overcame the coning issues observed with the Apparatus 2 paddle method, reduced variability and achieved complete release, whilst employing an accepted rotation speed of 100 rpm. The Apparatus 1 (basket) using a rotation speed of 100 rpm has therefore been selected as the QC Volume To confirm the media volume, an investigation was conducted using the Apparatus 1 (basket), 100 rpm with 500 mL and 900 mL of dissolution media pH 6.8. FIG. 2 displays the dissolution profile generated for the Emcitate FCP (Batch EF0078) in 500 mL plotted against the profiles generated in 900 mL media. Data represents mean of n=6.

The rate of drug release from Emcitate FCP was similar when using 500 ml or 900 mL volume, with complete dissolution being achieved within 15 minutes. The volume to be used for the QC method for Emcitate FCP was set to 500 mL. Use of the smallest feasible volume maximize final analyte concentration which aids analysis.

Proposed QC Dissolution Method

Based on the data generated, Apparatus 2 (paddle) at standard operating speeds (50 and 75 rpm) was not considered suitable for controlling Emcitate FCP due to the coning observed in the dissolution vessels. Apparatus 1 (basket) at 100 rpm achieved complete release in 15 minutes. Although complete solubility is expected in both pH 4.5 and pH 6.8 media, the Emcitate FCP demonstrated slower and incomplete release at pH 4.5 versus pH 6.8. Therefore, a pH 6.8 phosphate buffer was selected as the suitable dissolution media. The volume was set to 500 mL to use the smallest feasible volume to maximize final analyte concentration to aid analysis.

Based on the data presented, the proposed QC Dissolution method is summarized in Table 3.

TABLE 3

Summary of proposed QC dissolution method parameters for Emcitate FCP.

| Parameter | Details |
|---|---|
| Apparatus | Apparatus 1 (basket) |
| Media Volume | 500 mL |
| Dissolution Media | pH 6.8 phosphate buffer |
| Rotation Speed | 100 rpm |
| Temperature | 37° C. |

Assay Method for Dissolved Tiratricol

The chromatographic conditions for determining tiratricol have been further developed in this method as compared to the conditions used for Emcitate-DEV. The chromatographic conditions selected for Emcitate FCP are presented below.

Chromatographic Conditions

Column: Halo-C18 column, 50×3.0 mm, 2.7 μm, or equivalent.

Flow-rate: 0.75 mL/min

Injection volume: 100 μL

Column temperature: 40° C.

Detection wavelength: 226 nm

Mobile phase A: 10 mM ammonium formate+0.1% formic acid

Mobile phase B: Acetonitrile+0.1% formic acid

Gradient:

| Time (min) | % A | % B |
|---|---|---|
| 0.00 | 80 | 20 |
| 1.00 | 80 | 20 |
| 6.00 | 10 | 90 |

-continued

| Gradient: | | |
|---|---|---|
| Time (min) | % A | % B |
| 7.50 | 10 | 90 |
| 7.51 | 0 | 100 |
| 8.00 | 0 | 100 |
| 8.01 | 80 | 20 |
| 13.00 | 80 | 20 |

The amount of tiratricol released from the Emcitate tablets is expressed as percent of label claim.

Method Validation Results

- Specificity: No interference from dissolution medium or from tablet excipients.
- Linearity: Tiratricol response is linear in the range 0.07 to 0.85 μg/mL. (10% to 120% of nominal content). R2=0.9999
- Range: 0% to 120% of nominal content
- Accuracy: Accuracy was tested at 50%, 80% and 120% of nominal content. Recoveries of spikes to dissolution medium containing placebo and sampling after 30 minutes were between 97% and 101%.
- Precision: Repeatability: RSD between 0.0% and 3.0%.
- Intermediate precision: RSD between 1.0% and 2.0%.
- LoQ: LOQ set to 0.02 μg/mL. (Corresponding to 2.9% dissolution.) S/N ratio 84.

The validation was successful for all parameters. It was concluded that the analytical method was appropriate for its intended use.

Discriminatory Power of Proposed QC Dissolution Method

A risk assessment according to ICH Q8 Pharmaceutical development and ICH Q9 Quality risk management, was performed. Based on the outcome, one CMA and one CPP for Emcitate FCP were selected to be varied to investigate the ability of the proposed QC to discriminate. Hence, Emcitate was manufactured with tiratricol of two different particle size, D(95)<8.4 μm and D (95)<18.2 μm, from the supplier Dottikon, Emcitate batches EF0078 and EF0079, respectively. Drug substance from the previous tiratricol supplier DiverChim (D(100)<8.9 μm) was also included for comparison (batch EF0080). Additionally, the CPP, tableting compression force, was varied to generate tablets of different tablet hardness. Batch P0554 (primary stability batch) was compressed at (6 kN, 10 kN and 15.5 kN) generating tablets of hardness 41 N, 68 N and 104 N, respectively.

Typically, and according to regulatory recommendations (e.g. USP<1092>) the critical attributes are to be varied±20% for testing the dissolution method's discriminatory power. In the performed investigation the largest particle size of tiratricol was more than doubled as compared to particle size normally produced (i.e. within the specification criteria) and for the achieved tablet hardness it was varied by ±50%.

Figure 3:
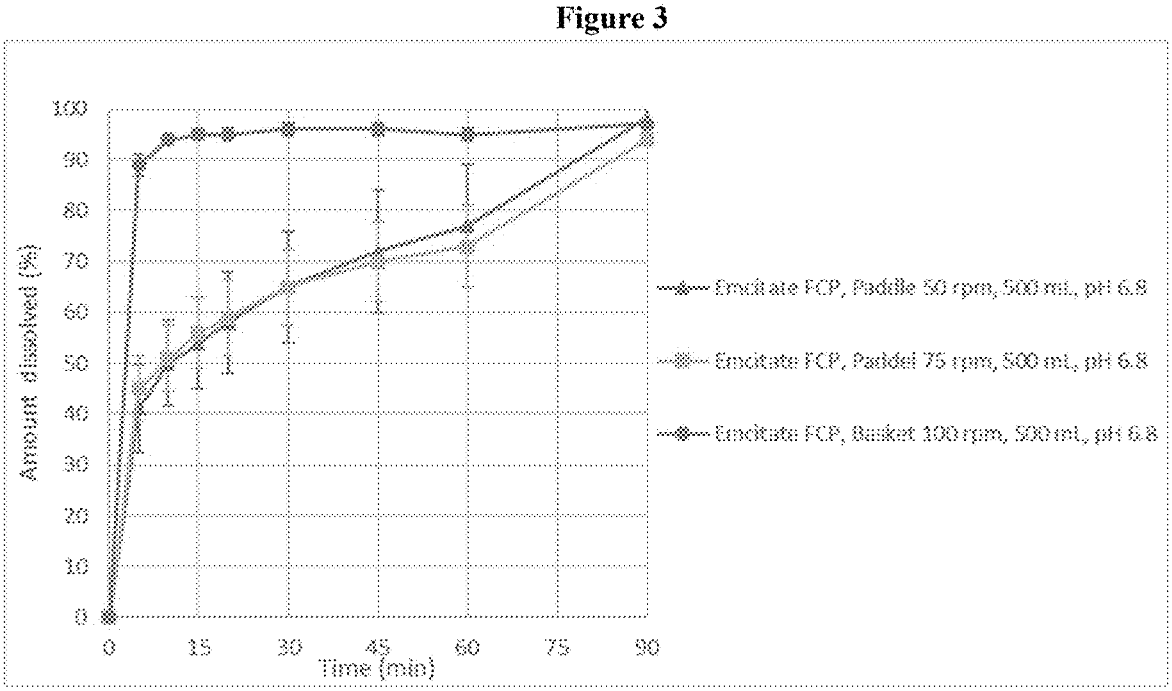
FIG. 3 shows the dissolution comparison of Emcitate FCP (Batch EF0078) in Apparatus 2 50 rpm and 75 rpm and Apparatus 1 100 rpm in 500 m mL pH 6.8 media (n=6).

Dissolution profiles for Emcitate FCP batches with different tiratricol particle size are shown in FIG. 3. In the particle size range tested no impact on the dissolution rate was observed. It is likely attributed to the rapid disintegrating nature of Emcitate FCP and the still quite small particle size although the tiratricol used in EF 0079 is considerably out of specification (D(95)≤10 μm) for the commercial drug substance.

Figure 4:
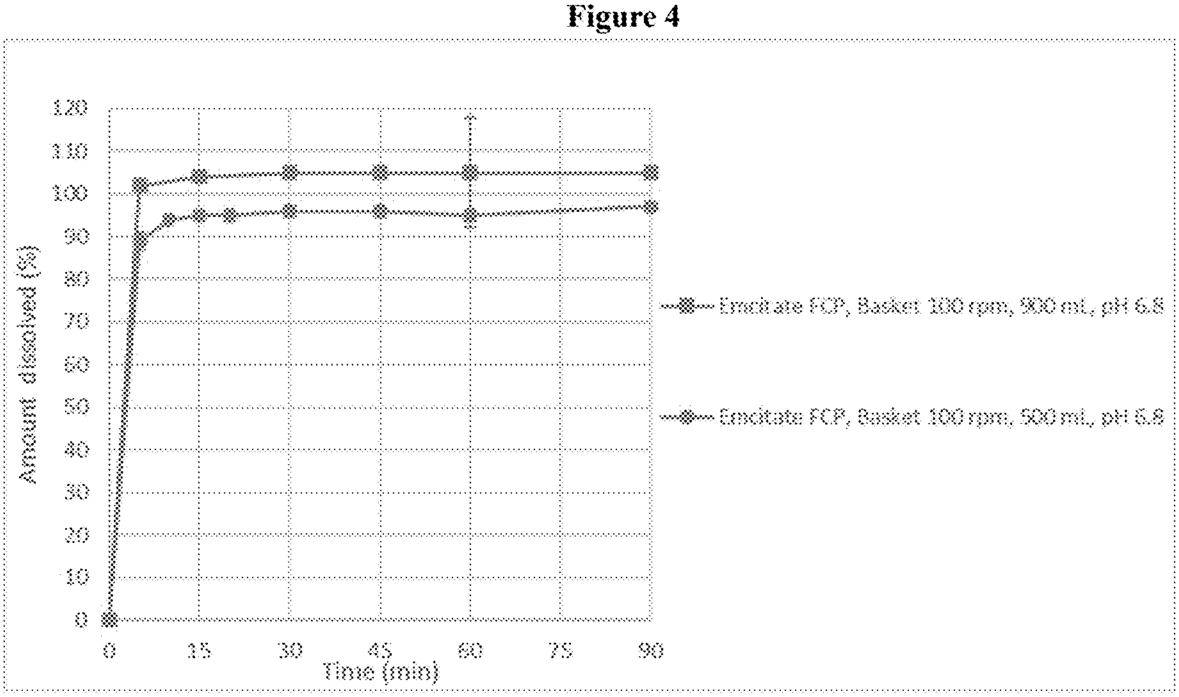
FIG. 4 shows dissolution comparison of the Emcitate FCP (EF0078) in pH 6.8 dissolution media 500 mL and 900 mL using Apparatus 1 at 100 rpm (n=6).
Figure 5:
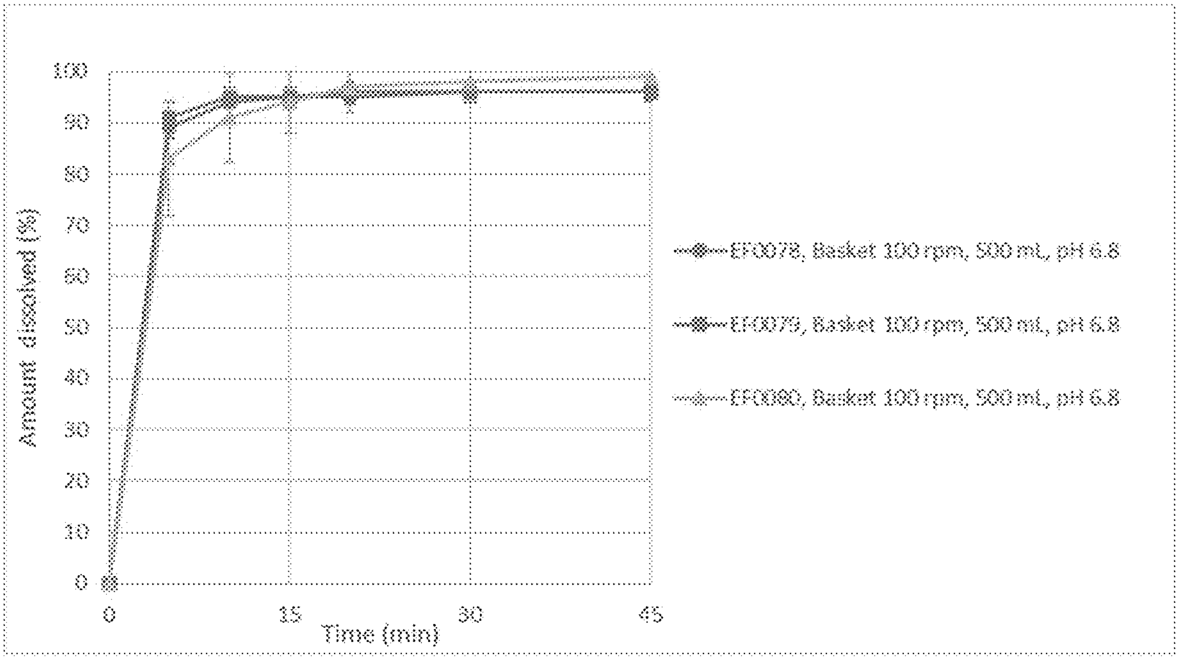
FIG. 5 shows dissolution profiles of Emcitate FCP, using different tiratricol particle size. EF0079, D (95)<8.4 μm, EF080 D (95)<18.2 μm and EF0080 D (100)<8.9. Tested with the proposed QC method (n=12).
Figure 6:
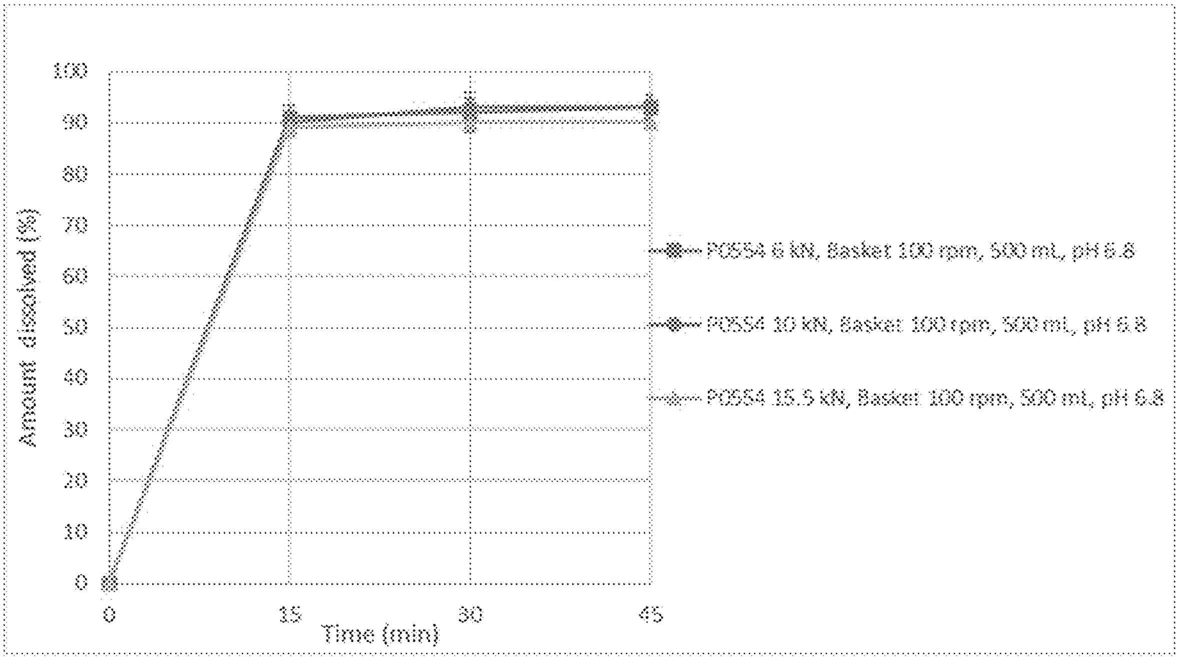
FIG. 6 shows dissolution of Emcitate FCP, (batch P0554) using different compression force generating different tablet hardness. Tested with the proposed QC method (n=12).
Figure 7:
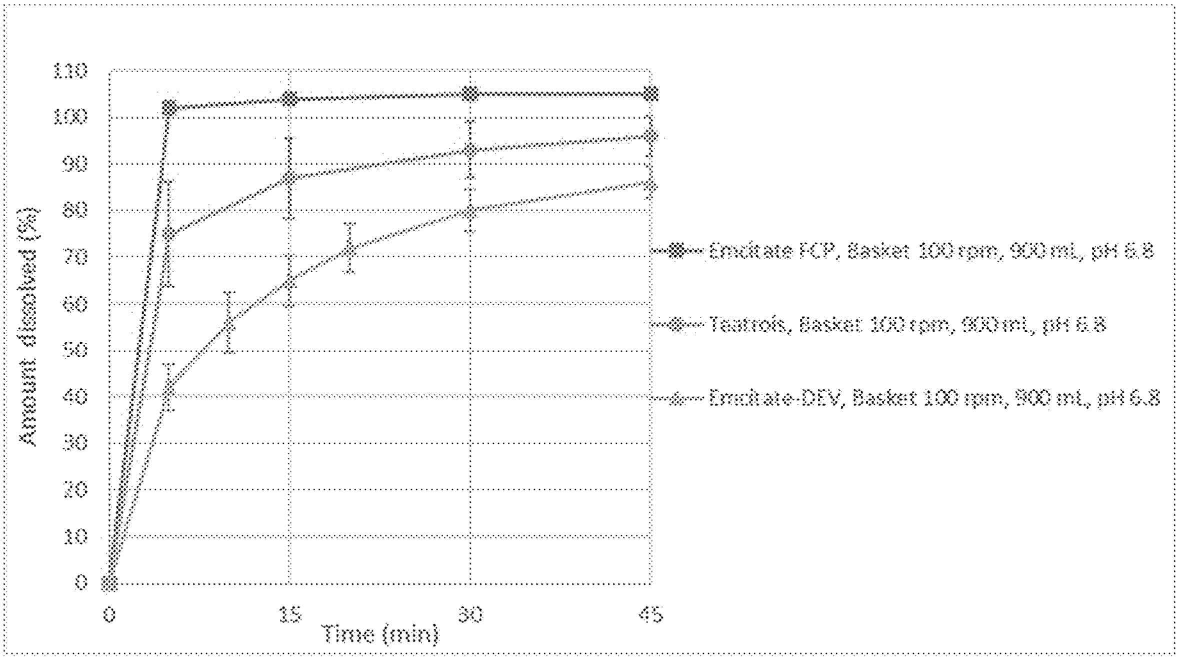
FIG. 7 shows dissolution Comparison of Teatrois, Emcitate-DEV and Emcitate FCP in the 900 mL pH 6.8 tested with Apparatus 1 (basket) at 100 rpm (n=6).

Dissolution profiles for batch P0554 (primary stability batch) that was compressed at different compression forces (6 kN, 10 kN and 15.5 kN) to generate tablets of different hardness are shown in FIG. 4. A wide range (±50%) of tablet hardness was achieved, i.e. 41 N, 68 N and 104 N. Despite the large difference in tablet hardness, no impact on the dissolution rate was observed. Even at the highest hardness Emcitate FCP disintegrates fast allowing for rapid dissolution During the development of the QC dissolution method the three tiratricol formulations; Teatrois, Emcitate-DEV and Emcitate FCP, were tested with the Apparatus 1 (basket) method, 100 rpm with 900 mL volume of pH 6.8 media. The dissolution profiles generated for these formulations are provided in FIG. 5. The method has the ability to discriminate between these products. Differences in the rate of dissolution are seen with Emcitate-DEV demonstrating the slowest rate of release and the Emcitate FCP demonstrating the fastest rate of release. Based on the similar dissolution of the Emcitate FCP in 500 mL and 900 mL pH 6.8 media (see FIG. 2), it is anticipated that a similar level of discrimination would be observed in 500 mL.

The proposed QC dissolution method has improved discriminatory power as compared to the method used for Emcitate-DEV. The pH 6.8 phosphate buffer media does possess discriminatory ability to detect differences in disintegration characteristics of the three formulations produced during the course of product development. Although, disintegration testing according to Ph. Eur. do not show significant differences between the formulations, visual observations in the dissolution baths show distinct different disintegration patterns. Similarity factor (F2) comparisons between the formulations failed to meet the passing criteria (i.e., F2≥50) (see Table). Hence, the tablet formulations are shown to be different from each other when tested with this method. However, it should be emphasized that the tablets are dispersed in a small volume of water before being administered to patients. Testing of suspensions from all three tablet formulations show equivalent dissolution profiles.

TABLE 4

F2 comparisons between Teatrois, Emcitate-DEV and Emcitate FCP

| Tiratricol formulation | F2 value |
|---|---|
| Teatrois vs Emcitate- DEV | 32.4 |
| Teatrois vs Emcitate FCP | 40.7 |
| Emcitate-DEV vs Emcitate FCP | 24.2 |

CONCLUSION

Emcitate FCP has been developed to assure rapid disintegration to facilitate dispersion in a small volume of water before administration to patients. For a tablet with the very rapid disintegration as shown for Emcitate FCP, it is difficult to vary CMA and CPP in a meaningful manner so that dissolution is impacted. When deliberately manufacturing Emcitate FCP tablets of different hardness, the disintegration is still so rapid that the dissolution method cannot distinguish between the batches. An increase in particle size of tiratricol to outside of the proposed specification criteria (D(95)≤10 μm) is not impacting the dissolution profile either. The development to set the dissolution method parameter has included all relevant aspects and based on that, the proposed QC dissolution method is regarded as suitable despite that discrimination has not been shown.

It can be noted that that the proposed QC dissolution method can discriminate between formulations of tiratricol used during development that visually show different disintegration behavior in the dissolution vessels. However, when these tablets are dispersed in water as is done for administration to patients, the suspensions show similar behavior in vitro.

The QC dissolution method parameters are summarized below.

Apparatus: Apparatus 1 (baskets)
Rotation Speed 100 rpm
Media Volume: 500 mL
Dissolution Media: pH 6.8 phosphate buffer
Temperature: 37° C.

Example 3

A Phase I, single-dose, randomized, blinded, five-period cross-over study in healthy adult male subjects (N=30) with six treatments (A-F; Table 6) was conducted with the primary objective to establish bioequivalence between 350 μg tiratricol FCP tablets and 350 μg tiratricol DEV tablets in a fasted state (Treatments A and B).

FCP tablet=Final commercial product (oblong shape)

DEV tablet=used in development phase (round shape)

Secondary objectives included to estimate the effect of food by comparing both 175 μg and 1050 μg tiratricol FCP tablet doses in fasted versus fed states (Treatment C vs. D, and Treatment E vs. F); to assess dose-proportionality of tiratricol FCP tablets in a fasted state (Treatment E vs. B vs. C).

TABLE 5

| Trt | Tiratricol dose | Tablet | Administered Dose | Prandial state | Planned number of subjects |
|---|---|---|---|---|---|
| A | 350 μg | DEV | 1 × 350 μg tablet | Fasted | 30 |
| B | 350 μg | FCP | 1 × 350 μg tablets | Fasted | 30 |
| C | 1050 μg | FCP | 3 × 350 μg tablets | Fasted | 25 |
| D | 1050 μg | FCP | 3 × 350 μg tablets | Fed | 20 |
| E | 175 μg | FCP | 0.5 × 350 μg tablet | Fasted | 25 |
| F | 175 μg | FCP | 0.5 × 350 μg tablet | Fed | 20 |

The primary objective was met, establishing bioequivalence between 350 μg tiratricol DEV tablets and 350 μg tiratricol FCP tablets in terms of Cmax and overall exposure AUC parameters.

TABLE 6

| Assessment of bioequivalence (PK analysis set) | | | | | |
|---|---|---|---|---|---|
| | Treatment A Tiratricol 350 μg DEV, fasted | | Treatment B Tiratricol 350 μg FCP, fasted | | Ratio |
| Parameter | n[a] | GLSMean[b] | n[a] | GLSMean[b] | (90% CI)[c] |
| Cmax (nmol/L) | 29 | 14.6 | 28 | 15.4 | 1.05 (0.94-1.18) |
| AUC (nmol. h/L) | | | | | |
| (0-72) | 29 | 29.3 | 28 | 30.4 | 1.04 (0.97-1.11) |
| (0-last) | 29 | 23.8 | 28 | 25.2 | 1.06 (1.00-1.12) |
| (0-inf) | 8 | 31.6 | 14 | 30.1 | 0.95 (0.86-1.06) |

Overall tiratricol exposure for the AUC (0-72) and AUC (0-last) parameters was comparable between the fasted and fed state (Treatment C vs. D and Treatment E vs. F; Table 4).

Tiratricol absorption was rapid in the fasted state (Treatments C and E, median Tmax 0.5 h) but slower in the fed state (Treatments D and F, median Tmax 1.25 h and 1.5 h, respectively).

In assessing dose proportionality after 175 μg, 350 μg, and 1050 μg doses (Treatments E: 175 μg (oblong, fasted), B: 350 μg (oblong, fasted), and C: 1050 μg (oblong, fasted), respectively), Cmax increased proportionally with increasing tiratricol dose For AUC (0-72) and AUC (0-last), exposure increased slightly more than dose proportionally. Dose proportionality after 175 μg, 350 μg, and 1050 μg doses (FCP, fasted): Cmax increased proportionally with increasing tiratricol dose, β=0.987, 90% CI (0.932, 1.043)

Figure 8:
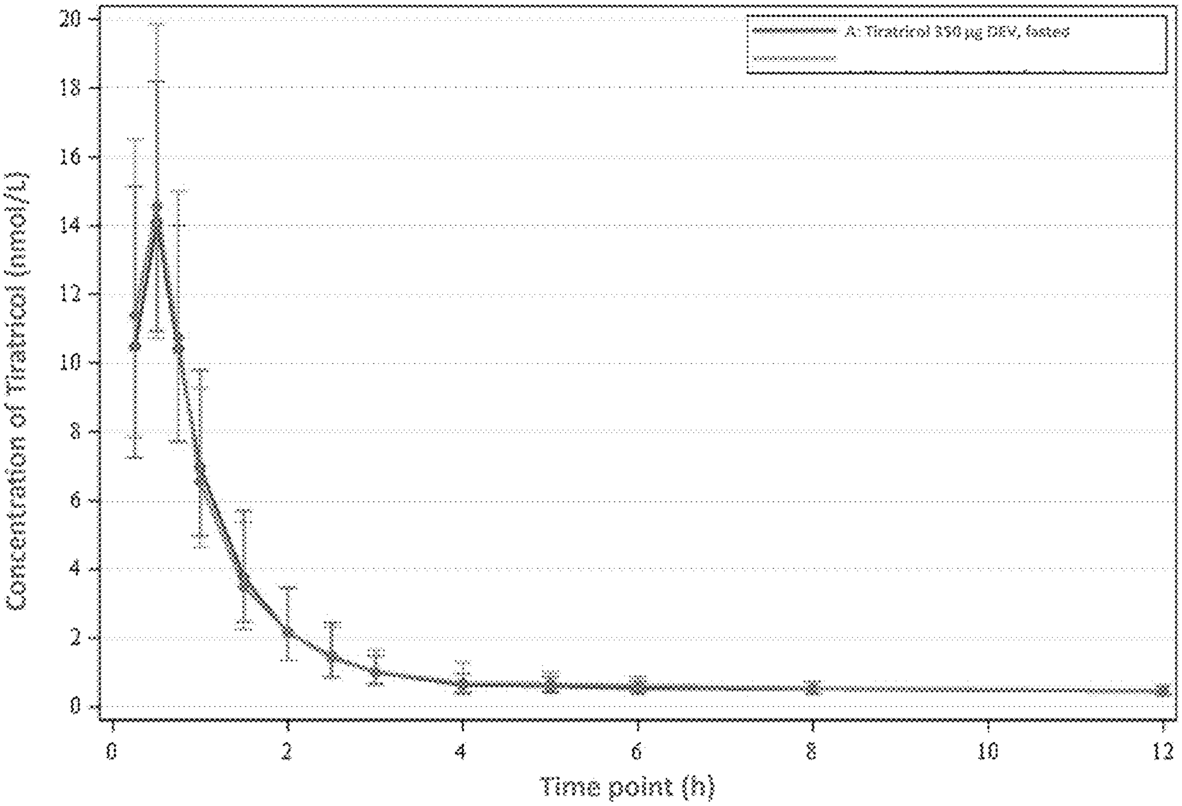
FIG. 8 shows shows the geometric mean (×/÷ geometric SD) serum tiratricol concentrations following treatment: Treatment A vs. B, fasted to 12 h post-dose: PK analysis set.

For AUC (0-72) and AUC (0-last), exposure increased slightly more than dose proportionally with β=1.098 90% CI (1.046, 1.150) and β=1.184 90% CI (1.146, 1.221), respectively FIG. 8 shows the geometric mean (×/÷geometric SD) serum tiratricol concentrations following treatment: Treatment A vs. B, fasted to 12 h post-dose: PK analysis set.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A pharmaceutical composition comprising:

about 0.2% compound 1, or a pharmaceutically acceptable salt thereof,

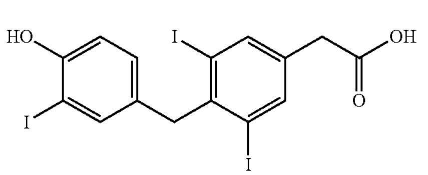

(1)

about 67% to about 77% calcium hydrogen phosphate anhydrous;

about 15% maize starch;

about 5% to about 15% lactose monohydrate; and about 2% to about 3% magnesium stearate.

2. The pharmaceutical composition of claim 1, wherein compound 1, or a pharmaceutically acceptable salt thereof, is present in an amount of about 350 μg, based on the weight of the free acid.

3. The pharmaceutical composition of claim 1, wherein the calcium hydrogen phosphate anhydrous is present in an amount of about 72%.

4. The pharmaceutical composition of claim 1, wherein the lactose monohydrate is present in an amount of about 10%.

5. The pharmaceutical composition of claim 1, wherein the magnesium stearate is present in an amount of about 2.5%.

6. The pharmaceutical composition of claim 1, wherein compound 1, or a pharmaceutically acceptable salt thereof, is micronized.

7. The pharmaceutical composition of claim 6, having a particle size D (95)≤10 μm.

8. The pharmaceutical composition of claim 1, wherein the pharmaceutical composition is a tablet.

9. The pharmaceutical composition of claim 8, wherein the pharmaceutical composition is an uncoated tablet.

10. The pharmaceutical composition of claim 8, wherein the tablet is oblong.

11. The pharmaceutical composition of claim 10, wherein the tablet has score lines on both sides.

12. The pharmaceutical composition of claim 11, having one or more of the following properties:

the mass loss after split is less than 3.0%, the friability of the split is not more than 1.0%, the split dissolution and the complete tablet are similar.

13. The pharmaceutical composition of claim 1, having a content uniformity of between about 95% and about 105%.

14. The pharmaceutical composition of claim 1, wherein the pharmaceutical composition dissolves in 10 minutes or less under the following parameters: 100 rpm rotation speed; 500 mL volume of a dissolution media that is pH 6.8 phosphate buffer, at 37° C.

15. A method of treating Allan-Herndon-Dudley syndrome in an individual, comprising administering to the individual in need thereof, a therapeutically acceptable amount of a pharmaceutical composition of claim 1.

16. The method of claim 15, wherein the pharmaceutical composition is suspended in water prior to administration.

17. The method of claim 15, wherein the pharmaceutical composition is administered as a dose, said dose being administered individually based on serum TSH levels, (F) T4 and T3 levels of the individual.

18. The method of claim 15, wherein the pharmaceutical composition is administered based on one of the following dose schedules:

350 μg once daily, or

350 μg twice daily, or

350 μg three times daily, or three doses daily, each selected from doses of 350 μg or 750 μg, or a total daily dose of least 2450 μg, delivered in increments of 350 μg or 700 μg.

19. The pharmaceutical composition of claim 1 wherein the calcium hydrogen phosphate anhydrous is present in an amount of about 72%, the lactose monohydrate is present in an amount of about 10%, and the magnesium stearate is present in an amount of about 2.5%.

* * * * *